(12) United States Patent
Pearce et al.

(10) Patent No.: US 11,851,205 B2
(45) Date of Patent: Dec. 26, 2023

(54) AIR QUALITY MONITORING

(71) Applicant: Honeywell International Inc., Charlotte, NC (US)

(72) Inventors: Daniel Pearce, Chard (GB); Timothy Lippold, Huntington Beach, CA (US); Spiros Sideris, Richmond Hill, CA (US); Jan Ludvik, Jesenice (CZ); Giorgio C. Isella, Culver City, CA (US)

(73) Assignee: Honeywell International Inc., Charlotte, NC (US)

( * ) Notice: Subject to any disclaimer, the term of this patent is extended or adjusted under 35 U.S.C. 154(b) by 253 days.

(21) Appl. No.: 17/304,798

(22) Filed: Jun. 25, 2021

(65) Prior Publication Data

US 2022/0001999 A1 Jan. 6, 2022

Related U.S. Application Data

(60) Provisional application No. 63/048,585, filed on Jul. 6, 2020.

(51) Int. Cl.
*B64D 45/00* (2006.01)
*B64D 13/06* (2006.01)
(Continued)

(52) U.S. Cl.
CPC ............ *B64D 45/00* (2013.01); *B64D 13/06* (2013.01); *B64F 5/60* (2017.01); *G01N 33/0063* (2013.01);
(Continued)

(58) Field of Classification Search
CPC .................. B64D 45/00; B64D 13/06; B64D 2013/0603; B64D 2045/0085;
(Continued)

(56) References Cited

U.S. PATENT DOCUMENTS 9,336,353 B2 5/2016 Valdes et al.
9,447,985 B2 9/2016 Johnson, Jr.
(Continued)

FOREIGN PATENT DOCUMENTS

CA 2924663 A1 9/2017
CA 3043996 A1 2/2018
(Continued)

OTHER PUBLICATIONS

Communication pursuant to Article 94(3) EPC from counterpart European Application No. 21182949.4 dated Feb. 10, 2023, 6 pp.
(Continued)

*Primary Examiner* — Mussa A Shaawat
(74) *Attorney, Agent, or Firm* — Shumaker & Sieffert, P.A.

(57) ABSTRACT

In some examples, a computing device is configured to monitor an air quality of a vehicle cabin by at least receiving, from a plurality of remote sensors distributed throughout the cabin, signals indicative of one or more air quality parameters for air in the cabin. Based on the received signals, the computing device can determine if values for the one or more air quality parameters are indicative of an air quality event and generate an output in response to such a determination. The output may include, for example, an audio or visual indication of the air quality event or a signal to control another system of the aircraft to take action to remedy the air quality event.

20 Claims, 4 Drawing Sheets

(51) Int. Cl.
*B64F 5/60* (2017.01)
*G01N 33/00* (2006.01)

(52) U.S. Cl.
CPC .............. *B64D 2013/0603* (2013.01); *B64D 2045/0085* (2013.01)

(58) Field of Classification Search
CPC ....... B64D 13/00; B64F 5/60; G01N 33/0063; G01N 33/0004; G01N 15/06; G01N 33/0039; G01N 33/004; G01N 33/0047
See application file for complete search history.

(56) References Cited

U.S. PATENT DOCUMENTS

| | | | |
|---|---|---|---|
| 9,723,987 | B2 | 8/2017 | Goetz |
| 10,043,363 | B2 | 8/2018 | Riedel et al. |
| 10,295,457 | B1 | 5/2019 | Ocheltree |
| 10,335,075 | B2 | 7/2019 | Vanslyke et al. |
| 10,503,942 | B1* | 12/2019 | Thurston .............. G06F 11/3006 |
| 10,871,756 | B2 | 12/2020 | Johnson, Jr. et al. |
| 10,908,578 | B2 | 2/2021 | Johnson, Jr. et al. |
| 10,921,768 | B2 | 2/2021 | Johnson, Jr. et al. |
| 11,156,978 | B2 | 10/2021 | Johnson, Jr. et al. |
| 11,326,800 | B2* | 5/2022 | Schindler ............ G01N 33/0004 |
| 2005/0104724 | A1* | 5/2005 | Faltesek ................. G08B 29/12 340/506 |
| 2010/0223020 | A1 | 9/2010 | Goetz |
| 2013/0030718 | A1* | 1/2013 | Williams ............ G01N 15/0618 702/24 |
| 2013/0116958 | A1 | 5/2013 | Kristensson et al. |
| 2013/0151618 | A1* | 6/2013 | Schmit ................. H04L 41/0803 709/204 |
| 2013/0327891 | A1* | 12/2013 | Zhang .................... B64D 13/08 244/118.5 |
| 2016/0214723 | A1* | 7/2016 | Fox ........................ B64D 13/06 |
| 2016/0214724 | A1 | 7/2016 | Fox et al. |
| 2016/0318613 | A1* | 11/2016 | Ludvik .............. B01D 53/0462 |
| 2018/0118351 | A1 | 5/2018 | Fox et al. |
| 2018/0148180 | A1* | 5/2018 | Fagundes ................ B64D 13/00 |
| 2018/0186212 | A1 | 7/2018 | Kundu et al. |
| 2018/0266856 | A1 | 9/2018 | Broadley et al. |
| 2018/0346130 | A1 | 12/2018 | Jouper |
| 2019/0100318 | A1* | 4/2019 | Space .................... B01D 53/72 |
| 2019/0173885 | A1 | 6/2019 | Barreras et al. |
| 2019/0187115 | A1 | 6/2019 | Bartosz et al. |
| 2020/0033017 | A1* | 1/2020 | Brown ............... G01N 33/0009 |
| 2020/0256571 | A1 | 8/2020 | Johnson, Jr. et al. |
| 2021/0356927 | A1 | 11/2021 | Johnson, Jr. et al. |
| 2021/0399911 | A1* | 12/2021 | Jorasch ............... H04L 12/1822 |

FOREIGN PATENT DOCUMENTS

| | | |
|---|---|---|
| CN | 103499948 A | 1/2014 |
| CN | 107976722 A | 5/2018 |
| EP | 3640138 A1 | 4/2020 |
| KR | 20150107325 A | 9/2015 |
| WO | 2016189420 A1 | 12/2016 |
| WO | 2020039379 A1 | 2/2020 |
| WO | 2020159893 A1 | 8/2020 |
| WO | 2020174462 A1 | 9/2020 |

OTHER PUBLICATIONS

Extended Search Report from counterpart European Application No. 21182949.4 dated Dec. 1, 2021, 13 pp.
Johnson Jr. et al., "CoolingLogic: Mosaic Christian Church A Case Study", Johnson Solid State, LLC, Feb. 2, 2019, 140 pp.
Johnson Jr., "A Method to Increase HVAC System Efficiency And Decrease Energy Consumption", CoolingLogic, Sep. 24, 2016, 51 pp.
Johnson Jr., "CoolingLogic: Changing the Way You Cool", Johnson Solid State, LLC, Nov. 7, 2018, 12 pp.
U.S. Appl. No. 16/921,401, filed Jul. 6, 2020, naming inventors Fox et al.
Committee on Air Quality in Passenger Cabins of Commercial Aircraft, Board on Environmental Studies and Toxicology, Division on Earth and Life Studies, National Research Council, "The Airliner Cabin Environment and the Health of Passengers and Crew," National Academy Press, (Applicant points out, in accordance with MPEP 609.04(a), that the year of publication, 2002, is sufficiently earlier than the effective U.S. filing date, so that the particular month of publication is not in issue.) , 2002, 345 pp.
Hall Jr. et al., "Monitoring Aircraft Cabin Particulate Matter Using a Wireless Sensor Network," American Institute of Aeronautics and Astronautics, Boise State University, Scholar Works, DOI:10.2514/6.2013-3345, Jul. 14, 2013, 18 pp.
Response to Extended Search Report dated Dec. 1, 2021, from counterpart European Application No. 21182949.4 filed Feb. 28, 2022, 11 pp.
Response to Communication pursuant to Article 94(3) EPC dated Feb. 10, 2023, from counterpart European Application No. 21182949.4 filed May 30, 2023, 17 pp.

* cited by examiner

AIR QUALITY MONITORING

This application claims the benefit of US Provisional Patent Application 63/048,585, filed 6 Jul. 2020, the entire content of which is incorporated herein by reference.

TECHNICAL FIELD

This disclosure generally relates to systems and methods for monitoring the air quality in a vehicle, such as in a cabin of an aircraft.

BACKGROUND

An environmental control system provides pressurized air to a cabin of an aircraft. This pressurized air may be supplied from a variety of sources, such as bleed air from an engine, a cabin air compressor (CAC), or an auxiliary power unit (APU).

SUMMARY

In some examples, a plurality of air quality sensors can be distributed throughout a vehicle (e.g., an aircraft cabin or a cabin of another type of vehicle) to sense values for one or more air quality parameters. The sensors can be wired or wireless (e.g., for data communication and/or power). The sensors can be networked and configured to transmit data (either wired or wirelessly) to a centralized processing device in the vehicle (e.g., an aircraft) or external to the vehicle.

According to one example, a method of monitoring air quality includes receiving, at a centralized processing device and from a plurality of sensors located in a vehicle, signals indicative of values for one or more air quality parameters for air in the vehicle; and generating an output based on the values for the one or more air quality parameters.

According to another example, a system includes receiver circuitry configured to receive, from a plurality of sensors located in a vehicle, values for one or more air quality parameters for air in the vehicle; and processing circuitry configured to generate an output based on the values for the one or more air quality parameters.

According to another example, a system includes receiver circuitry configured to receive, from each sensor of a plurality of sensors located in a cabin of an aircraft, respective signals indicating a level of carbon dioxide (CO2) in air in the cabin; and processing circuitry configured to: determine that a signal from at least one sensor of the plurality of sensors indicates that the level of CO2 in the air in the cabin is greater than or equal to a threshold level; and in response to determining that the signal from the at least one sensor indicates that the level of CO2 in the air in the cabin is greater than or equal to the threshold level, generate an output comprising one or more of a visual warning indicator or an audible warning indicator.

The details of one or more examples are set forth in the accompanying drawings and the description below. Other features, objects, and advantages will be apparent from the description and drawings, and from the claims.

DETAILED DESCRIPTION

Various examples are described below that are generally directed to apparatuses, methods, systems, and computer program products, that relate to a network of sensing devices affixed to the interior of a vehicle, such as an aircraft, a road vehicle, or a marine vessel. While aircraft are primarily referred to herein, in other examples, the example apparatuses, methods, systems, and computer program products described herein may be used with other types of vehicles.

Some environmental control systems (ECSs) in aircraft utilize sensors within the airflow path of the ECS to help ensure that the ECS is not introducing undesirable gases, such as carbon monoxide (CO), or other types of contamination from outside the aircraft cabin into the aircraft cabin through the outlet air vents of the ECS. Other than smoke detectors, however, aircraft typically do not include sensors inside the aircraft cabin to detect contamination that may be originating from inside the cabin. Due to this lack of sensors, pilots, flight crew, and maintenance staff do not have real-time air quality information at their disposal during flight.

According to aspects of this disclosure, a plurality of air quality sensors can be distributed throughout an aircraft cabin to sense one or more various air quality parameters and generate outputs indicative of the one or more air quality parameters. The sensor can include sensing circuitry and be, for example, configured to generate an output (e.g., referred to herein as a signal) indicative of a value of the respective air quality parameter. In this way, the sensors may be referred to as measuring a value of the air quality parameter.

The sensors can be wired or wireless (e.g., for data communication and/or power). The sensors can be networked and configured to transmit data (either wired or wirelessly) to a centralized processing device (also referred to herein as a centralized data processing device in some examples) in the aircraft or external to the aircraft. In some examples, the centralized processing device may be included in one or more of the sensors or be distributed across multiple sensors. In flight, the centralized processing device can aggregate and analyze the data to provide an air quality status to flight crew and/or to alert the flight crew to certain air quality events. As one example, an air quality event may be the level of a certain compound in the air of the cabin being greater than or equal to a predetermined threshold value that is determined to represent an undesirably high level for the certain compound. As another example, an air quality event may be the level of a different compound in the air of the cabin being less than or equal to a predetermined threshold value that is determined to represent an undesirably low level for the different compound. Examples of air quality parameters that can be sensed include carbon dioxide (CO2), carbon monoxide (CO), ozone (O3), temperature, volatile organic compounds (VOCs), ultrafine particles (UFPs), humidity, or any combination thereof.

As one example, passengers inside an aircraft may emit CO2 by breathing. Thus, having more passengers in the cabin may result in higher levels of CO2 in the cabin compared to having fewer passengers, or similarly, having more passengers in a specific region of the cabin may result in higher levels of CO2 for that specific region. Additionally, having passengers moving around the cabin, breathing heavily, coughing sneezing, or the like may also cause elevated levels of CO2 in the aircraft cabin generally or at specific regions in the aircraft cabin. While these elevated levels may be unlikely to pose an immediate adverse impact to passengers, elevated levels of CO2 may be correlated with an environment in which disease or viruses are more likely to spread, or more generally, with congestion and/or poor ventilation inside the cabin which may result in the air being less comfortable and/or potentially having adverse effects on the health of a passenger.

As another example, the cabin may become polluted due to the inadvertent introduction of VOCs into the fresh air supply to the passenger compartment. This can occur, for example, when aircraft de-icing fluid is ingested into the aircraft engine during ground de-icing operations and is then drawn into the bleed air supply port. Pollutants can also be introduced into the fresh bleed air supply due to aircraft equipment failure or malfunctions, such as oil from an aircraft main engine or Auxiliary Power Unit (APU) that leaks past a compromised oil seal and is then ingested into the bleed supply ducting.

According to aspects of this disclosure, the centralized data processing device may be configured to receive, from one or more air quality sensors, values for one or more air quality parameters for air in the aircraft cabin and determine if the values for the one or more air quality parameters are indicative of an air quality event, such as an elevated level of CO2 or an elevated level of VOCs. The centralized data processing device can receive the values from the one or more air quality sensors in the form of a raw signal, a digitized signal, or any other suitable format. In response to detecting an air quality event, the central data processing device may generate one or more outputs, such as a recommending one or more courses of remedial action to the flight crew and/or be in communication with other flight systems to automatically initiate remedial action. In addition, in some examples, the central data processing device can cause a real-time indicator or alert to be provided to a flight crew in response to detecting an air quality event. The flight crew may then take remedial action to help mitigate the potential air quality issue detected by the central data processing device.

In some examples, the centralized data processing device can upload data acquired in-flight for additional post-flight processing. For example, the sensor data acquired in flight can be compared with other in-flight sensor data from other flights to detect deviations from normal that may be indicative of events such as upcoming maintenance issues (e.g., degraded filters or air inflow). In this way, the air quality sensors described herein may be used as a diagnostic device to facilitate maintenance operations of the aircraft or other vehicle.

Figure 1:
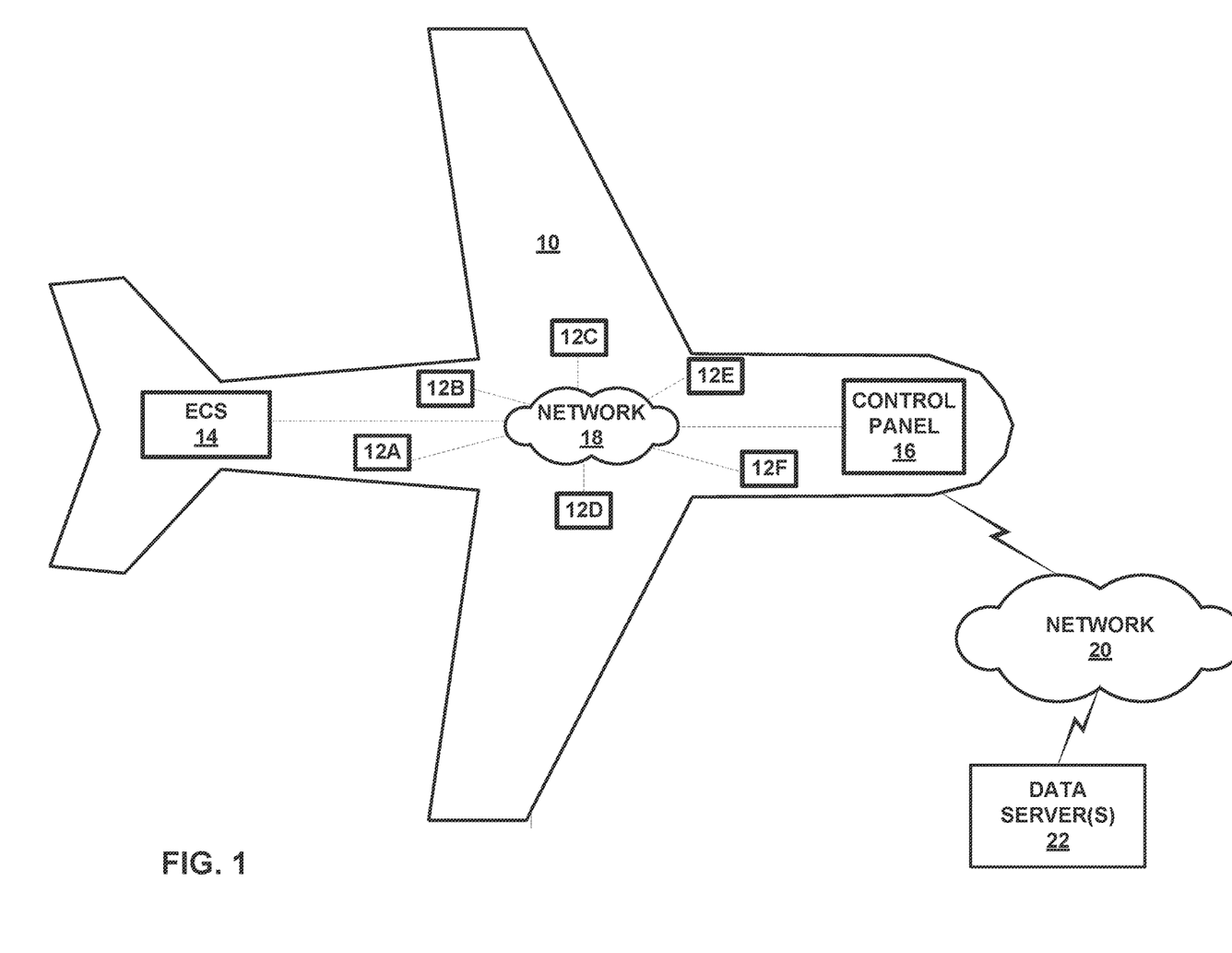
FIG. 1 is a conceptual block diagram depicting an example cabin air quality monitoring system, in accordance with aspects of this disclosure.

FIG. 1 is a conceptual block diagram of an example aircraft environment in which aircraft 10 includes a plurality of remote air quality sensors, shown in FIG. 1 as remote air quality sensors 12A-12F (also referred to as "sensors 12"). Although FIG. 1 shows six remote sensors, aircraft 10 may include a greater or a fewer number of remote sensors in other examples, such as two, three, four, five, or more than six sensors. Aircraft 10 also includes ECS 14 and control panel 16, which are configured to communicate with each other and with sensors 12 over network 18.

Although shown in FIG. 1 as having a fixed-wing form factor, aircraft 10 generally represents any sort of aircraft, and although the techniques of this disclosure may be used in conjunction with any sort of aircraft, the techniques described herein may be of particular benefit for passenger aircraft that include a cabin for passenger travel. Although various techniques of this disclosure will be described with respect to a passenger cabin of an airplane, it should be understood that the techniques are equally applicable to other compartments of other vehicles.

Sensors 12 may include any suitable air quality sensor, such as, but not limited to, one or more CO2 sensors, O3 sensors, CO sensors, temperature sensors, humidity sensors, VOC sensors, or any combination thereof. In some examples, sensors 12 may include one or more biosensors that include a biorecognition element that is configured to selectively react with a target analyte in the air to produce an electrical signal that is proportional to a concentration of the analyte. Sensors 12 may be distributed throughout the passenger cabin of aircraft 10, such that sensors 12 are positioned to sense air quality parameters of the air inside the cabin.

ECS 14 may, for example, be configured to control the general comfort and safety in the passenger cabin of aircraft 10 by, for instance, circulating conditioned air to the passenger cabin, as well as to various other portions of aircraft 10, such as the flight deck, galleys, other occupied compartments, cargo compartments, electronic equipment bays, and the like. ECS 14 may perform such operations to provide a certain level of air quality in the cabin by, for example, maintaining desired temperatures and humidity levels within the cabin of aircraft 10.

Control panel 16 represents any sort of centralized data processing device configured to receive and process values for one or more air quality parameters detected by sensors 12. Control panel 16 can be a specialized device, such as an application running on a computing device, such as a tablet, or can be integrated into an existing aircraft system, such as an aircraft cabin control system that controls the temperature, lighting, entertainment systems, and other aspects of passenger experience. In some examples, the functionality of control panel 16 may implemented into one of sensors 12 or distributed across multiple remote sensors of sensors 12.

Network 18 represents any suitable wired or wireless communications network by which control panel 16 can communicate with sensors 12. As examples of wired communications, control panel 16 may communicate with sensors 12 over direct wiring, twisted pair, fiber optic cable, coaxial cable, or the like. As examples of wireless communications standards, control panel 16 may communicated with sensors 12 using an IEEE 802.11 specification (e.g., WiFi™), an IEEE 802.15 specification (e.g., ZigBee™), a Bluetooth™ standard, or the like. In some instances, network 18 may also include any number of intermediary devices such as routers or switches.

In some examples, ECS 14 may also interface with control panel 16 via a controller of ECS 14. The controller of ECS 14 may, for example, be a computer having processing circuitry and a memory, configured to control an air purification subsystem and other subsystems of ECS 14. In some implementations, the controller of ECS 14 and control panel 16 may be highly integrated or even implemented in the same device.

In some examples, control panel 16 is configured to monitor air quality of a cabin in aircraft 10 based on values for one or more air quality parameters for air in the aircraft cabin received from and generated by sensors 12. Based on the values for the one or more air quality parameters, control panel 16 may determine if the values for the one or more air quality parameters are indicative of an air quality event, such as undesirably high level of CO2 or CO in the cabin. In some examples, control panel 16 may determine the existence of the air quality event based on any of an average of the values for the one or more air quality parameters received from sensors 12, a maximum of the values for the one or more air quality parameters received from sensors 12, a minimum of the values for the one or more air quality parameters received from sensors 12, or any other suitable technique. In some examples, control panel 16 may assign time stamps to each of the values for the one or more air quality parameters received from sensors 12, determine based on the time stamps a change in the one or more air quality parameters over a period of time, and generate the output based on (e.g., in response to) the change in the one or more air quality parameters over the period of time being greater than or equal to a threshold value.

Control panel 16 may then generate an output based on the values for the one or more air quality parameters or based on detecting the air quality event. In some examples, to generate the output, control panel 16 may be configured to generate a visual indicator, such as causing a light to illuminate or causing a display device to present a text-based warning. In some examples, to generate the output, control panel 16 may additionally or alternatively include sound generating circuitry configured to generate an audible indicator such as a sound. In response to the visual and/or audible indicator, a member of the cabin crew or a pilot may, for example, adjust operating parameters of ECS 14 to help mitigate the potential air quality issue detected by control panel 16. In some examples, control panel 16 may send an alert to a remote device, such as a ground station.

In some examples, in response to detecting the air quality event, control panel 16 may automatically, without immediate human intervention, generate an electronic signal to control ECS 14. Control panel 16 may, for example, cause ECS 14 to increase the amount of outside air being introduced into the cabin or to increase the overall ventilation rate of air in the cabin by at least turning on or increasing the speed of recirculation fans. In some examples, in response to detecting the air quality event, control panel 16 may generate an electronic signal to control an emergency safety system of the aircraft.

In some examples, each sensor of sensors 12 may be associated with a specific region of the cabin, and control panel 16 may generate an output for a specific region of the aircraft based on a sensor for that region indicating an air quality event for the region. For example, if only the values for the one or more air quality parameters from sensor 12B are indicative of an air quality event, then control panel 16 may be configured to generate a visual or audible indicator that specifically identifies the region of the cabin associated with sensor 12B. Control panel 16 may also, for example, additionally or alternatively cause ECS 14 to increase a circulation rate of air in the cabin only for the region of the cabin associated with sensor 12B. The association of particular sensors of sensors 12 with particular regions of the aircraft cabin may help control panel 16 and/or a flight crew more quickly ascertain a potential reason for the air quality event and/or more quickly take action to help address (e.g., eliminate) the air quality event or the adverse impact the air quality event may have on passengers in the particular region of the aircraft cabin.

Control panel 16 may be configured to store, during flight and/or during ground operations, the values for the one or more air quality parameters for the air in the aircraft cabin and transmit, either during flight or post flight via network 20, the values for the one or more air quality parameters to data servers 22. Data servers 22 may then aggregate the air quality parameters data obtained from aircraft 10 with air quality parameters data obtained from other aircraft. Based on a comparison of the air quality parameters data obtained from aircraft 10 with the aggregated air quality parameters data from the other aircraft, data servers 22 may, for example, analyze the health of ECS 14. If data servers 22, for example, determines that a level of a contaminant in the cabin of aircraft 10 was higher than other similarly situated flights, for example with a similar number of passengers, same type of aircraft, same route, and/or similar flight conditions, then data servers 22 may output maintenance recommendations, such as a list of items to be inspected.

Network 20 represents any suitable communication links between control panel 16 and data servers 22, including wireless communication links according to a cellular communication standard, such as 4G, 4G-LTE (Long-Term Evolution), LTE Advanced, 5G, or the like, or an IEEE 802.11 specification, an IEEE 802.15 specification (e.g., ZigBee™), a Bluetooth™ standard, or the like. Network 20 may also include any number of wired communication links and include intermediary devices such as routers and switches.

Figure 2:
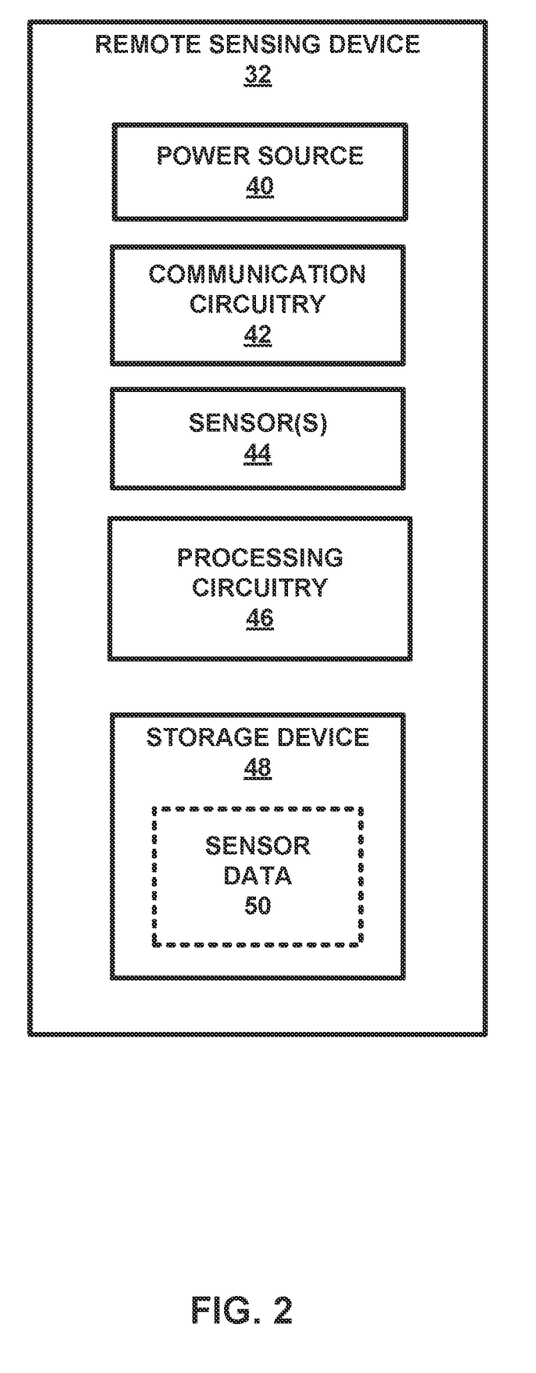
FIG. 2 is a conceptual block diagram of an example remote sensing device.

FIG. 2 is a conceptual block diagram of an example remote sensing device. In the example of FIG. 2, remote sensing device 32 includes power source 40, communication circuitry 42, sensors 44, processing circuitry 46, and storage device 48. Remote sensing device 32 is an example implementation of any of sensors 12 described above with respect to FIG. 1.

Power source 40 represents all sources of power for the various components of remote sensing device 32 and may include one or more batteries, one or more capacitors, circuitry for receiving alternating current (e.g., 115 volts of 230 volts), or circuitry for receiving direct current (e.g., 28 volts).

Communication circuitry 42 generally represents any one or more of wireless transmitters, wireless receivers, modems, wired networking components (e.g., Ethernet cards), wireless communication components that operate according to any of a variety of IEEE 802.11 standards, or other physical components for facilitating the communication over network 18 described above with respect to FIG. 1.

Sensors 44 generally represent the sensing capabilities of remote sensing device 32 and may include one or more of a CO2 sensor, an O2 sensor, an O3 sensor, a CO sensor, a temperature sensor, or a humidity sensor. Sensors 44 include any suitable sensing circuitry configured to sense the air quality parameter of interest. For example, sensors 44 may include any one or more of nondispersive infrared sensors, chemical-based sensors, electromechanical sensors, catalytic bead sensors, photoionization sensors, infrared point sensors, infrared imaging sensors, semiconductor-based sensors, ultrasonic sensors, or holographic sensors. In some examples, sensors 44 may include one or more biosensors, including electrochemical biosensors, optical biosensors, electronic biosensors, piezoelectric biosensors, gravimetric biosensors, or pyroelectric biosensors.

Processing circuitry 46 generally represents any of the circuitry of remote sensing device 32 needed to carry out any of the functionality described herein, and may include one or more microprocessors, digital signal processors (DSPs), application specific integrated circuits (ASICs), field programmable gate arrays (FPGAs), discrete logic, software, hardware, firmware, or any combinations thereof.

Storage device 48 represents any one or more of read only memory (ROM) or random access memory (RAM), including dynamic random access memory (DRAM), including synchronous DRAM (SDRAM), magnetoresistive RAM (MRAM), resistive RAM (RRAM). Storage device 48 may alternatively or additionally include optical disk storage, magnetic disk storage, or other magnetic storage devices, flash memory, or any other medium that can be used to store desired program code in the form of instructions or data structures and that can be accessed by a computer, such as control panel 16.

Storage device 48 may be configured to store sensor data 50, which represents the air quality parameter values obtained by sensors 44. In this regards, storage device 48 may represent a short term, temporary storage, such as a buffer that stores the air quality parameter values prior to transmission by communication circuitry 42, or may represent a longer term, non-volatile storage that that stores the air quality parameter values indefinitely for future processing.

Figure 3:
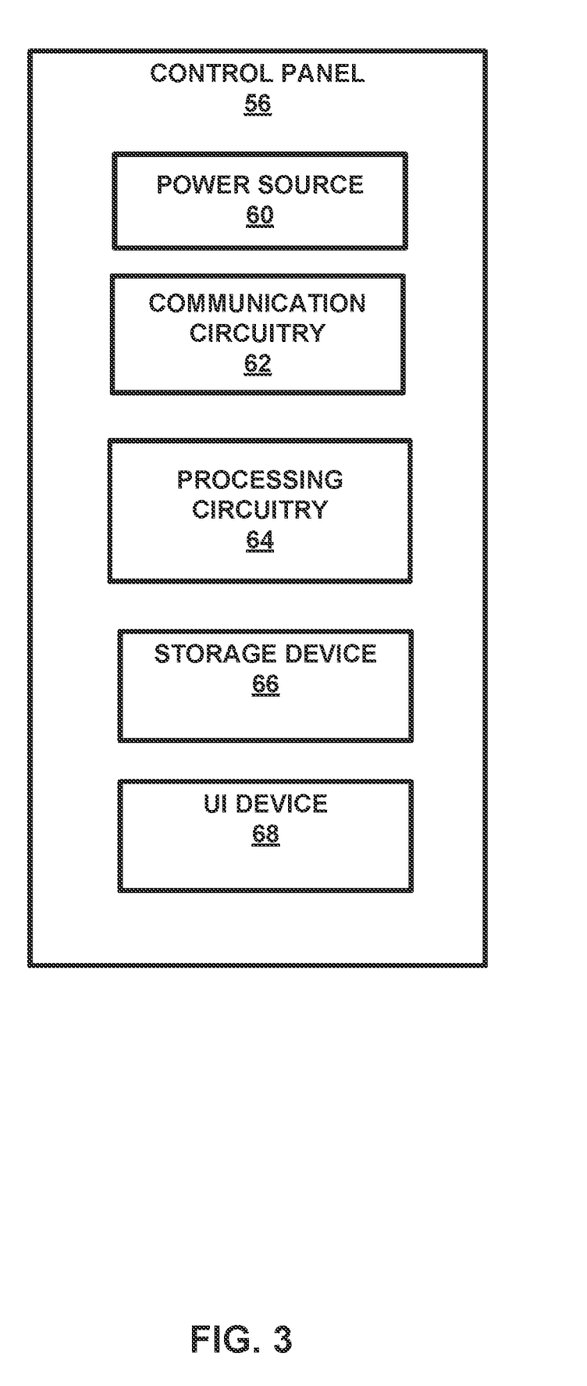
FIG. 3 is a conceptual block diagram of an example control panel device.

FIG. 3 is a conceptual block diagram of an example control panel device. In the example of FIG. 3, control panel 56 includes power source 60, communication circuitry 62, processing circuitry 64, storage devices 66, and user interface (UI) device 68. Control panel 56 is an example implementation of control panel 16 described above with respect to FIG. 1.

Power source 60 represents all sources of power for the various components of control panel 56 and may include one or more batteries, one or more capacitors, circuitry for receiving alternating current (e.g., 115 volts of 230 volts), or circuitry for receiving direct current (e.g., 28 volts).

Communication circuitry 62 generally represents any one or more of wireless transmitters, wireless receivers, modems, wired networking components (e.g., Ethernet cards), wireless communication components that operate according to any of a variety of IEEE 802.11 standards, or other physical components for facilitating the communication over network 18 described above with respect to FIG. 1. Communication circuitry 62 may also include components for communicating via a cellular communication standard, such as 4G, 4G-LTE (Long-Term Evolution), LTE Advanced, 5G, or the like. Via communication circuitry 62, control panel 56 may communicate with other systems and components onboard an aircraft as well as with systems off the aircraft, such as airport-based systems or other ground-based systems. Communication circuitry 62 may also include components for communicating, during flight, with other aircraft or ground-based systems.

Processing circuitry 64 generally represents any of the circuitry of remote sensing device 32 needed to carry out any of the functionality described herein, and may include one or more microprocessors, DSPs, ASICs, FPGAs, discrete logic, software, hardware, firmware, or any combinations thereof.

Storage device 66 represents any one or more of ROM or RAM, such as DRAM, including SDRAM, MRAM, RRAM. Storage device 66 may alternatively or additionally include optical disk storage, magnetic disk storage, or other magnetic storage devices, flash memory, or any other medium that can be used to store desired program code in the form of instructions or data structures.

UI device 68 may be any one or more of a display, indicator lights, a speaker, or any other such device for conveying information to a user of control panel 56. UI device 68 may, for example, be configured to output a visual warning indicator or an audible warning indicator in response to control panel 56 detecting an air quality event. UI device may also include user input components such as a keyboard, mouse, touchscreen display or the like. Although shown as part of control panel 56 in FIG. 3, UI device 68 may be physically separate from, but in communication with, the other components of control panel 56.

Figure 4:
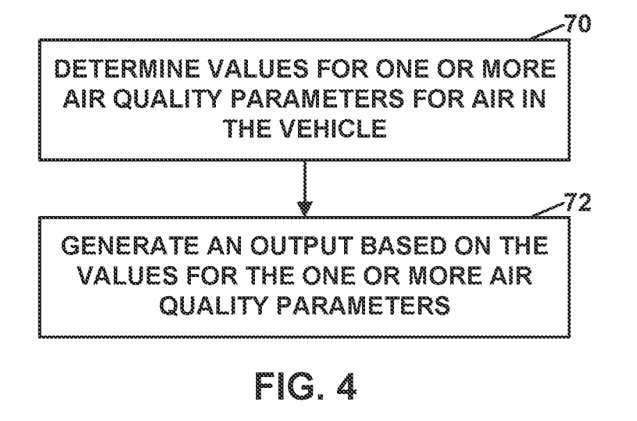
FIG. 4 is a flowchart illustrating an example process performed by a vehicle system of this disclosure.

FIG. 4 is a flowchart illustrating an example process performed by a vehicle system of this disclosure. The vehicle system determines values for one or more air quality parameters for air in the vehicle (70). The vehicle system may, for example, include a plurality of sensors (e.g., two, three, four or more sensors) such as sensors 12 and a centralized processing device such as control panel 16. The plurality of sensors may be configured to transmit, either via wires or wirelessly, signals indicating the values for the one or more air quality parameters for air in the vehicle to the centralized processing device. As described above, the one or more air quality parameters may include any one or more of an O3 level, a CO2 level, a CO level, a VOC level, a humidity level, or a temperature.

The vehicle system may generate an output based on the values for the one or more air quality parameters (72). As described above, the output may include any one or more of a visual warning indicator, an audible warning indicator, an electronic signal to control an environmental control system of the vehicle, or an electronic signal to control an emergency safety system of the vehicle.

Figure 5:
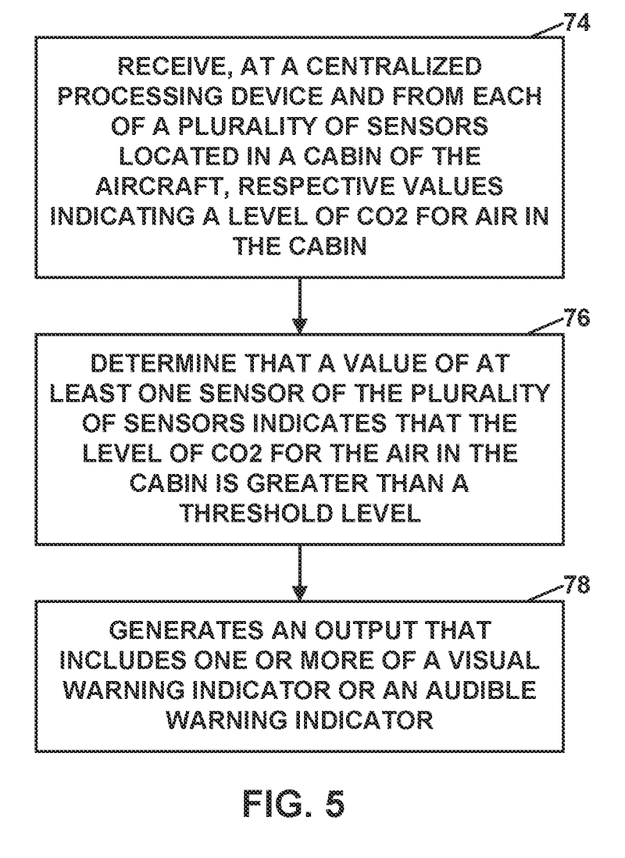
FIG. 5 is a flowchart illustrating an example process performed by a vehicle system of this disclosure.

FIG. 5 is a flowchart illustrating an example process performed by an aircraft system of this disclosure. While the system of FIG. 1 is primarily referred to in the description of FIG. 5, in other examples, a different system including a plurality of air quality sensors can perform the process of FIG. 5. The aircraft system receives, at a centralized processing device 16 and from each of a plurality of sensors 12 located in a cabin of the aircraft 10, respective values indicating a level of CO2 for air in the cabin (74). The plurality of sensors 12 may be configured to transmit, either via wires or wirelessly, the values indicating the level of CO2 for air in the cabin to the centralized processing device. The centralized processing device is primarily referred to as control panel 16 in the description of FIG. 5 but may be a different device in other examples.

Control panel 16 determines that a value of at least one sensor of the plurality of sensors 12 indicates that the level of CO2 for the air in the cabin is greater than or equal to a predetermined threshold level (76). In some examples, the respective values indicating the level of CO2 for the air in the cabin may be associated with timestamps, and the value of the at least one sensor of the plurality of sensors indicating the level of CO2 for the air in the cabin may represent a change in a level of CO2 for air in the cabin over a period of time. In some examples, the value of the at least one sensor of the plurality of sensors 12 indicating the level of CO2 for the air in the cabin may represent a level of CO2 for air in the cabin at a specific instance in time.

In response to determining that the value of the at least one sensor of the plurality of sensors indicates that the level of CO2 for the air in the cabin is greater than or equal to the threshold level, control panel 16 generates an output that includes one or more of a visual warning indicator or an audible warning indicator (78). The output may, for example, include an identification of a region associated with the at least one sensor having the value that indicates that the level of CO2 for the air in the cabin is greater or equal to than the threshold level. In response to determining that the value of the at least one sensor of the plurality of sensors indicates that the level of CO2 for the air in the cabin is greater than or equal to the threshold level, control panel 16 may cause, either automatically or based on a user input, ECS 14 of the aircraft to increase a circulation rate of air for a region of the aircraft associated with the at least one sensor having the value that indicates that the level of CO2 for the air in the cabin is greater than or equal the threshold level.

The following numbered clauses illustrate one or more aspects of the devices and techniques described in this disclosure.

Clause 1: A method of monitoring air quality, the method comprising: receiving, at a centralized processing device and from a plurality of sensors located in a vehicle, signals indicative of values for one or more air quality parameters for air in the vehicle; and generating an output based on the values for the one or more air quality parameters.

Clause 2: The method of clause 1, wherein the output comprises one or more of: a visual warning indicator; an audible warning indicator; an electronic signal to control an environmental control system of the vehicle; or an electronic signal to control an emergency safety system of the vehicle.

Clause 3: The method of clause 1 or 2, wherein the one or more air quality parameters comprises an ozone (O3) level, a carbon dioxide (CO2) level, a carbon monoxide (CO) level, a volatile organic compound level, a humidity level, or a temperature.

Clause 4: The method of any of clauses 1-3, wherein receiving the values for the one or more air quality parameters for air in the vehicle comprises wirelessly receiving the values for the one or more air quality parameters at the centralized processing device from the plurality of sensors located in the vehicle.

Clause 5: The method of any of clauses 1-4, further comprising: assigning time stamps to each of the values for the one or more air quality parameters; and determining based on the time stamps a change in the one or more air quality parameters over a period of time, wherein generating the output comprises generating the output based on the change in the one or more air quality parameters over the period of time being greater than or equal to a threshold value.

Clause 6: The method of any of clauses 1-5, wherein generating the output based on the values for the one or more air quality parameters comprises: determining the output is greater than or equal to a threshold value; and generating the output in response to determining the output is greater than or equal to the threshold value.

Clause 7: The method of any of clauses 1-6, wherein generating the output based on the values for the one or more air quality parameters comprises generating the output based on one or more of an average of the values for the one or more air quality parameters, a maximum of the values for the one or more air quality parameters, or a minimum of the values for the one or more air quality parameters.

Clause 8: The method of any of clauses 1-7, further comprising: during a flight of the vehicle, storing the values for the one or more air quality parameters for the air in the vehicle; and while the vehicle is on the ground, transmitting the values for the one or more air quality parameters to a processing device off the vehicle.

Clause 9: A system comprising: receiver circuitry configured to receive, from a plurality of sensors located in a vehicle, values for one or more air quality parameters for air in the vehicle; and processing circuitry configured to generate an output based on the values for the one or more air quality parameters.

Clause 10: The system of clause 9, wherein the plurality of sensors includes a first sensor and a second sensor, and wherein the values for the one or more air quality parameters include a first value for an air quality parameter from the first sensor and a second value for the air quality parameter from the second sensor.

Clause 11: The system of clause 9, wherein the plurality of sensors includes a first sensor and a second sensor, and wherein the values for the one or more air quality parameters include a first value for a first air quality parameter from the first sensor and a second value for a second air quality parameter from the second sensor, the first air quality parameter being different from the second air quality parameter.

Clause 12: The system of any of clauses 9-11, wherein the plurality of sensors comprises a first sensor located within a first region of the vehicle and a second sensor located within a second region of the vehicle that is different than the first region, and wherein generating the output based on the values for the one or more air quality parameters comprises generating an electronic signal to control an environmental control system for the first region of the vehicle based on a value of an air quality parameter detected by the first sensor.

Clause 13: The system of any of clauses 9-12, wherein the plurality of sensors comprise an ozone (O3) level, a carbon dioxide (CO2) sensor, a carbon monoxide (CO) sensor, a volatile organic compound level, a humidity sensor, or a temperature sensor.

Clause 14: The system of any of clauses 9-13, wherein the vehicle comprises an aircraft.

Clause 15: The system of any of clauses 9-14, wherein the processing circuitry is configured to generate the output by at least comparing one or more of the values for the one or more air quality parameters or a value determined based on the one or more of the values for the one or more air quality parameters to a threshold value, the system further comprising a memory storing the threshold value.

Clause 16: The system of any of clauses 9-15, further comprising the plurality of sensors.

Clause 17: A system comprising: receiver circuitry configured to receive, from each sensor of a plurality of sensors located in a cabin of an aircraft, respective signals indicating a level of carbon dioxide (CO2) in air in the cabin; and processing circuitry configured to: determine that a signal from at least one sensor of the plurality of sensors indicates that the level of CO2 in the air in the cabin is greater than or equal to a threshold level; and in response to determining that the signal from the at least one sensor indicates that the level of CO2 in the air in the cabin is greater than or equal to the threshold level, generate an output comprising one or more of a visual warning indicator or an audible warning indicator.

Clause 18: The system of clause 17, wherein the output comprises an identification of a region associated with the at least one sensor.

Clause 19: The system of clause 17 or 18, wherein the processing circuitry is further configured to: cause an environmental control system of the aircraft to increase a circulation rate of air for a region of the aircraft associated with the at least one sensor.

Clause 20: The system of any of clauses 17-19, wherein the respective values indicating the level of CO2 for the air in the cabin are associated with timestamps, and the value of the at least one sensor of the plurality of sensors indicating the level of CO2 for the air in the cabin comprises a change in a level of CO2 for air in the cabin over a period of time.

The various electronic devices described in this disclosure may be implemented as one or more ASICs, as a magnetic nonvolatile RAM or other types of memory, a mixed-signal integrated circuit, a central processing unit (CPU), an FPGA, a microcontroller, a programmable logic controller (PLC), a system on a chip (SoC), a subsection of any of the above, an interconnected or distributed combination of any of the above, or any other type of component or one or more components capable of performing the techniques described herein.

Functions executed by electronics associated with the devices systems described herein may be implemented, at least in part, by hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in electronics included systems described herein. The terms "processor," "processing device," or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, functionality ascribed to the devices and systems described herein may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure. The computer-readable medium may be non-transitory.

Various aspects of the disclosure have been described. These and other aspects are within the scope of the following claims.

What is claimed is:

1. A method of monitoring air quality, the method comprising:
   receiving, at a centralized processing device and from a plurality of sensors located in a vehicle, signals indicative of values for one or more air quality parameters for air in the vehicle;
   assigning, by the centralized processing device, time stamps to each of the values for the one or more air quality parameters;
   determining, by the centralized processing device and based on the time stamps, a change in the one or more air quality parameters over a period of time;
   comparing, by the centralized processing device, the change in the one or more air quality parameters over the period of time against a threshold value; and
   generating, by the centralized processing device, an output based on a determination by the centralized processing device that the change in the one or more air quality parameters is greater than or equal to a threshold value.

2. The method of claim 1, wherein the output comprises one or more of:
   a visual warning indicator; or
   an audible warning indicator.

3. The method of claim 1, wherein the one or more air quality parameters comprises an ozone (O3) level, a carbon dioxide (CO2) level, a carbon monoxide (CO) level, a volatile organic compound level, a humidity level, or a temperature.

4. The method of claim 1, wherein receiving the values for the one or more air quality parameters for air in the vehicle comprises wirelessly receiving the values for the one or more air quality parameters at the centralized processing device from the plurality of sensors located in the vehicle.

5. The method of claim 1, wherein generating the output comprises generating, by the centralized processing device, the output based on one or more of a change, over the period of time, in an average of the values for the one or more air quality parameters, a maximum of the values for the one or more air quality parameters, or a minimum of the values for the one or more air quality parameters.

6. The method of claim 1, further comprising:
   during a flight of the vehicle, storing the values for the one or more air quality parameters for the air in the vehicle; and
   while the vehicle is on ground, transmitting the values for the one or more air quality parameters to a processing device off the vehicle.

7. The method of claim 1, wherein the signals indicative of values for the one or more air quality parameters for air in the vehicle comprises a first set of signals, and wherein the method further comprises:
   receiving, by the centralized processing device a second set of signals indicative of values for the one or more air quality parameters for one or more other vehicles;
   comparing, by the centralized processing device, the first set of signals against the second set of signals; and
   based on a determination by the centralized processing device that the first set of signals deviates from the second set of signals, generating a maintenance recommendation.

8. A system comprising:
   receiver circuitry configured to receive, from a plurality of sensors located in a vehicle, values for one or more air quality parameters for air in the vehicle; and
   processing circuitry configured to:
   assign time stamps to each of the values for the one or more air quality Parameters;
   determine, based on the time stamps, a change in the one or more air quality parameters over a period of time;
   compare the change in the one or more air quality parameters over the period of time against a threshold value; and
   generate an output based on a determination that the change in the one or more air quality parameters is greater than or equal to the threshold value.

9. The system of claim 8, wherein the plurality of sensors includes a first sensor and a second sensor, and wherein the values for the one or more air quality parameters include a first value for an air quality parameter from the first sensor and a second value for the air quality parameter from the second sensor.

10. The system of claim 8, wherein the plurality of sensors includes a first sensor and a second sensor, and wherein the values for the one or more air quality parameters include a first value for a first air quality parameter from the first sensor and a second value for a second air quality parameter from the second sensor, the first air quality parameter being different from the second air quality parameter.

11. The system of claim 8, wherein the plurality of sensors comprises a first sensor located within a first region of the vehicle and a second sensor located within a second region of the vehicle that is different than the first region, and
   wherein generating the output based on a determination that the change in the one or more air quality parameters is greater than or equal to the threshold value comprises generating an electronic signal to control an environmental control system for the first region of the vehicle based on changes in values of an air quality parameter detected by the first sensor over the period of time.

12. The system of claim 8, wherein the plurality of sensors comprise an ozone (O3) level, a carbon dioxide (CO2) sensor, a carbon monoxide (CO) sensor, a volatile organic compound level, a humidity sensor, or a temperature sensor.

13. The system of claim 8, wherein the vehicle comprises an aircraft.

14. The system of claim 8, further comprising the plurality of sensors.

15. The system of claim 8,
   wherein the values for the one or more air quality parameters comprise a first set of values for the one or more air quality parameters,
   wherein the receiver circuitry is configured to receive a second set of values for the one or more air quality parameters for air in one or more other vehicles, and
   wherein the processing circuitry is configured to:
      compare the first set of values against the second set of values; and
      generate a maintenance recommendation based on a determination that the first set of values deviates from the second set of values.

16. The system of claim 8, wherein the output comprises one or more of:
   a visual warning indicator; or
   an audible warning indicator.

17. A system comprising:
   receiver circuitry configured to receive, from at least one sensor of a plurality of sensors located in a cabin of an aircraft, respective signals indicating levels of carbon dioxide (CO2) in air in the cabin; and
   processing circuitry configured to:
      assign time stamps to each of the levels of CO2;
      determine, based on the time stamps, a change in CO2 level over a period of time;
      determine that the change in CO2 level is greater than or equal to a threshold value; and
      in response to determining that the change in CO2 level is greater than or equal to the threshold value, generate an output comprising one or more of a visual warning indicator or an audible warning indicator.

18. The system of claim 17, wherein the output comprises an identification of a region associated with the at least one sensor.

19. The system of claim 17, wherein the processing circuitry is further configured to:
   cause an environmental control system of the aircraft to increase a circulation rate of air for a region of the aircraft associated with the at least one sensor.

20. The system of claim 17,
   wherein the levels of CO2 in the air in the cabin comprises a first set of CO2 levels,
   wherein the receiver circuitry is configured to receive a second set of CO2 levels for air in cabins of one or more other vehicles, and
   wherein the processing circuitry is configured to:
      compare the first set of CO2 levels against the second set of CO2 levels; and
      generate a maintenance recommendation based on a determination that the first set of CO2 levels deviates from the second set of CO2 levels.

* * * * *